United States Patent [19]

Montzka et al.

[11] 4,228,285
[45] Oct. 14, 1980

[54] 14-HYDROXY-6-OXAMORPHINANS AND 14-HYDROXY-6-OXAISOMORPHINANS

[75] Inventors: Thomas A. Montzka, Manlius; John D. Matiskella; Richard A. Partyka, both of Liverpool, all of N.Y.

[73] Assignee: Bristol-Myers Company, New York, N.Y.

[21] Appl. No.: 16,050

[22] Filed: Feb. 28, 1979

[51] Int. Cl.$^2$ ................ C07D 491/18; A61K 31/435
[52] U.S. Cl. .................................... 546/63; 424/256; 424/260; 546/15
[58] Field of Search .................................. 546/63, 15

[56] References Cited

U.S. PATENT DOCUMENTS

| | | | |
|---|---|---|---|
| 3,819,635 | 6/1974 | Pachter | 260/285 |
| 3,853,889 | 12/1974 | Monkovic et al. | 424/267 |
| 3,959,290 | 5/1976 | Monkovic et al. | 260/293.55 |
| 4,016,167 | 4/1977 | Montzka et al. | 260/293.55 |

OTHER PUBLICATIONS

Lambert et al., Chem. Abs. 88, 62495r (1977).

*Primary Examiner*—Mark L. Berch
*Attorney, Agent, or Firm*—Richard R. Lloyd

[57] ABSTRACT

14-Hydroxy-6-oxamorphinans and 14-hydroxy-6-oxaisomorphinans optionally substituted in the 3-, 7- and 17-positions have been found to possess potent analgetic, narcotic antagonist, antitussive and/or ADH inhibitory activity. The compounds are prepared by total synthesis and are not derived from opium alkaloids.

16 Claims, No Drawings

14-HYDROXY-6-OXAMORPHINANS AND 14-HYDROXY-6-OXAISOMORPHINANS

SUMMARY OF THE INVENTION

14-Hydroxy-6-oxamorphinans and 14-hydroxy-6-oxaisomorphinans of the formula

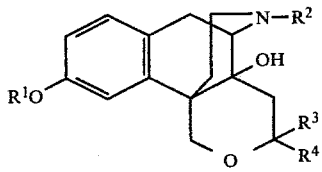

wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl,

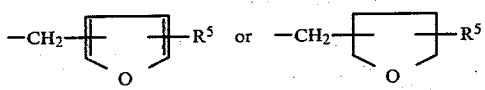

in which $R^5$ is hydrogen or (lower)alkyl, and $R^3$ and $R^4$ are the same or different and are hydrogen or (lower)alkyl, or $R^3$ and $R^4$, when taken together with the carbon atom to which they are attached, represent a spiroalkyl group of from 3 to 7 carbon atoms; and pharmaceutically acceptable salts thereof, possess analgetic, narcotic antagonist antitussive and/or ADH inhibitory activity, or are useful intermediates in the preparation of such compounds.

DESCRIPTION OF THE PRIOR ART

U.S. Pat. No. 3,853,889 discloses substituted 8-oxamorphinans and 8-oxaisomorphinans having the formula

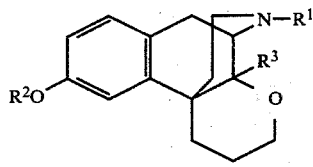

wherein $R^1$ is H, (lower)alkyl, (lower)alkenyl,

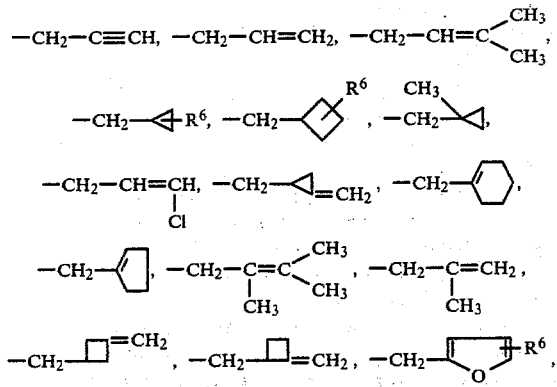

-continued

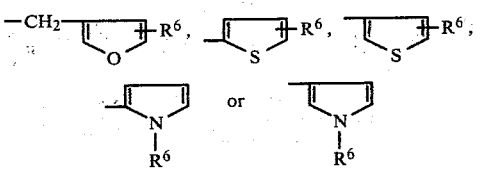

in which $R^6$ is H or $CH_3$; $R^2$ is H, (lower)alkyl, (lower)alkanoyl, cinnamoyl,

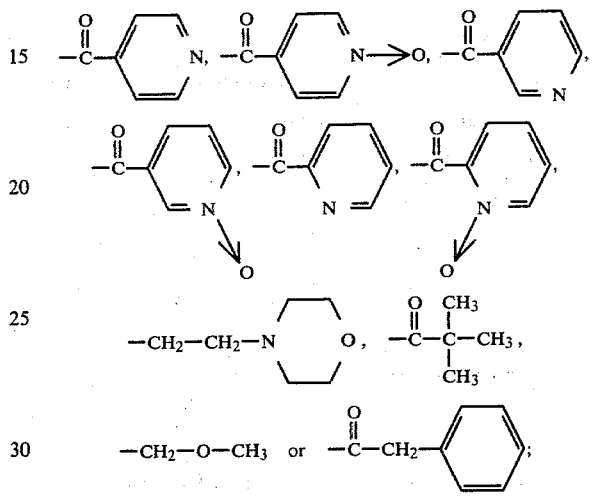

and $R^3$ is H or (lower)alkyl; and pharmaceutically acceptable acid addition salts thereof. The compounds are stated to be analgetic agents, narcotic antagonists or intermediates in the preparation of such agents. U.S. Pat. No. 3,959,290, a continuation-in-part of the above-identified patent, has a substantially identical disclosure.

U.S. Pat. No. 4,016,167 discloses substituted 6,8-dioxamorphinans and 6,8-dioxaisomorphinans having the formula

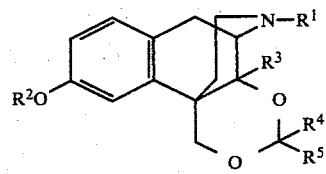

wherein $R^1$ is H, (lower)alkyl, (lower)alkenyl,

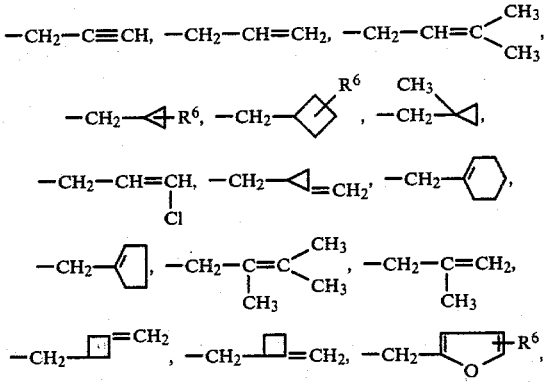

-continued

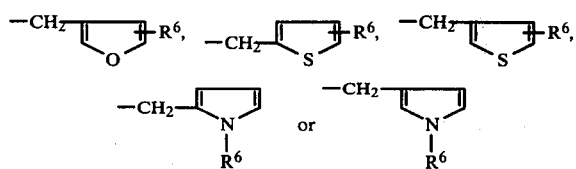

in which R⁶ is H or CH₃; R² is H, (lower)alkyl, (lower)alkanoyl, cinnamoyl,

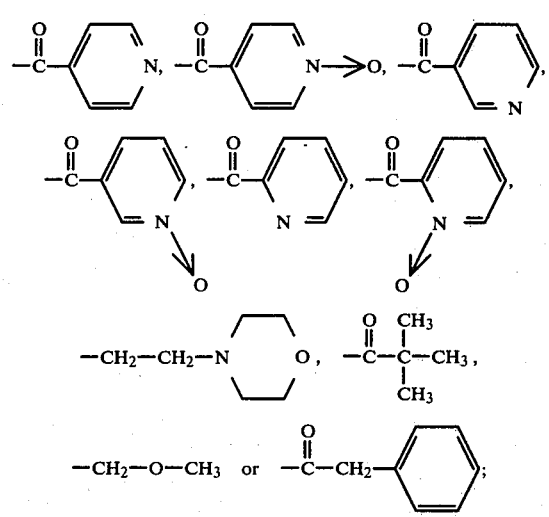

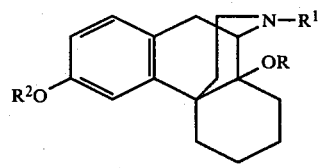

or

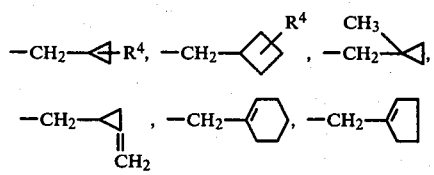

R³ is H or (lower)alkyl; and R⁴ and R⁵ are alike or different and each is H, (lower)alkyl or trifluoromethyl, or when taken together R⁴ and R⁵ are a carbonyl function or a spiroalkyl group of 3 to 7 carbon atoms; and pharmaceutically acceptable acid addition salts thereof. The compounds are stated to possess analgetic agonist-/antagonist activity or to be useful intermediates. Other prior art is cited in columns 1-4 of this patent.

U.S. Pat. No. 3,819,635 discloses 3,14,17-trisubstituted morphinans and isomorphinans of the formula

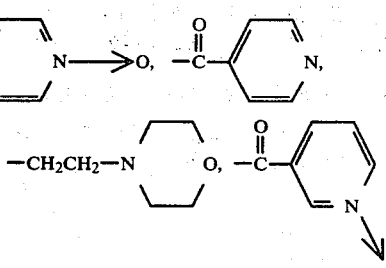

wherein R¹ is propargyl, allyl, 3,3-dimethylallyl, 3-chloroallyl,

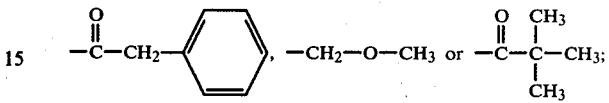

or (lower)alkenyl, in which R⁴ is H or CH₃; R² is hydrogen, (lower)acyl, (lower)alkyl,

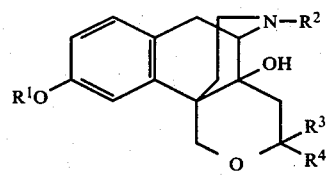

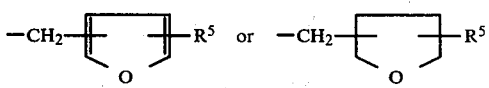

and R is hydrogen, (lower)acyl, trichloroacetyl or cinnamoyl; and nontoxic pharmaceutically acceptable salts thereof. The compounds are analgetics and/or narcotic antagonists.

COMPLETE DISCLOSURE

This invention relates to substituted 14-hydroxy-6-oxamorphinans and 14-hydroxy-6-oxaisomorphinans of the formula wherein R¹ is hydrogen, (lower)alkyl, (lower)alkanoyl or nicotinoyl; R² is hydrogen, (lower)alkyl, propargyl, allyl, 3,3-dimethylallyl, cyclopropylmethyl, cyclobutylmethyl, in which R⁵ is hydrogen or (lower)alkyl, and R³ and R⁴ are the same or different and are hydrogen or (lower)alkyl, or R³ and R⁴, when taken together, represent an alkylene group of from 2 to 6 carbon atoms; and pharmaceutically acceptable salts thereof, and to their total synthesis from the known compound, 6-carbomethoxy-8-methoxy-3-methyl-11-oxo-1,2,3,4,5,6-hexahydro-2,6-methano-3-benzazocine[5-carbomethoxy-2'-methoxy-2-methyl-9-oxo-6,7-benzomorphan].

Drug abuse by thrill-seeking youth or by people looking for an escape from the realities of everyday life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new nonaddicting analgetics and/or narcotic antagonists.

It was therefore an object of the present invention to find novel low abuse analgetics and/or narcotic antagonists. It was a further object of the present invention to develop a method of synthesis that would not be dependent upon opium alkaloids as starting materials.

The objects of the present invention have been met by the provision of the compounds of Formula I and by their total synthesis from 6-carbomethoxy-8-methoxy-3-methyl-11-oxo-1,2,3,4,5,6-hexahydro-2,6-methano-3-benzazocine.

The compounds of Formula I have the basic 6-oxamorphinan nucleus which is numbered and represented by the following plane formula:

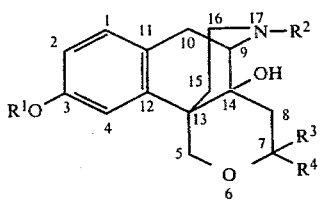

When $R^3$ and $R^4$ are alike, there are three asymmetric carbon atoms in the morphinan molecule (carbons 9, 13 and 14), which result in two diastereoisomeric racemates (four optical isomers) because the iminoethano system attached to carbons 9 and 13 is geometrically constrained to a cis-1,3-diaxial fusion. However, when $R^3$ and $R^4$ are not alike, then carbon 7 also becomes asymmetric. This results in four diastereoisomeric racemates or a total of eight optical isomers.

The present invention includes both the 6-oxamorphinans and the 6-oxaisomorphinans, either as their diastereoisomeric and/or d,l (racemic) mixtures or as their resolved optical isomers. The d- and l-isomers may be separated and isolated by fractional crystallization of the diastereoisomeric salts formed by the reaction of the racemic mixture with, for instance, d- or l-tartaric acid or D-(+)-α-bromocamphorsulfonic acid. Alternatively, one may obtain the desired d- or l- form of a compound of Formula I by utilizing the pure d- or l- form of the starting 6-carbomethoxy-8-methoxy-3-methyl-11-oxo-1,2,3,4,5,6-hexahydro-2,6-methano-3-benzazocine. The 6-oxamorphinans are the preferred series of compounds and the (−)-isomers of the compounds are the preferred isomers.

In a preferred embodiment of this invention the compounds have the structure of Formula I in which $R^1$ is hydrogen or (lower)alkyl, $R^2$ is hydrogen, (lower)alkyl, cyclopropylmethyl or cyclobutylmethyl, and $R^3$ and $R^4$ are the same or different and are hydrogen or (lower)alkyl.

In a more preferred embodiment of this invention the compounds have the structure of Formula I in which $R^1$ is hydrogen or methyl, $R^2$ is hydrogen, methyl, cyclopropylmethyl or cyclobutylmethyl, and $R^3$ and $R^4$ are the same or different and are hydrogen or methyl.

In a most preferred embodiment of this invention, the compounds have the structure of Formula I in which $R^1$, $R^3$ and $R^4$ are hydrogen and $R^2$ is cyclopropylmethyl (and most preferably the (−)-isomer thereof).

In another most preferred embodiment of this invention, the compounds have the structure of Formula I in which $R^1$, $R^3$ and $R^4$ are hydrogen and $R^2$ is cyclobutylmethyl (and most preferably the (−)-isomer thereof).

In another most preferred embodiment, the compounds have the structure of Formula I in which $R^1$ is hydrogen and $R^2$, $R^3$ and $R^4$ are methyl (and most preferably the (−)-isomer thereof).

In another most preferred embodiment of this invention, the compounds have the structure of Formula I in which $R^1$ is hydrogen, $R^3$ and $R^4$ are methyl, and $R^2$ is cyclobutylmethyl (and most preferably the (−)-isomer thereof).

In another most preferred embodiment of this invention, the compounds have the structure of Formula I in which $R^1$ is hydrogen, $R^3$ and $R^4$ are methyl, and $R^2$ is cyclopropylmethyl (and most preferably the (−)-isomer thereof).

The compounds of this invention are prepared by a total synthesis comprising multiple steps, as outlined in Chart I for some of the preferred embodiments of this invention.

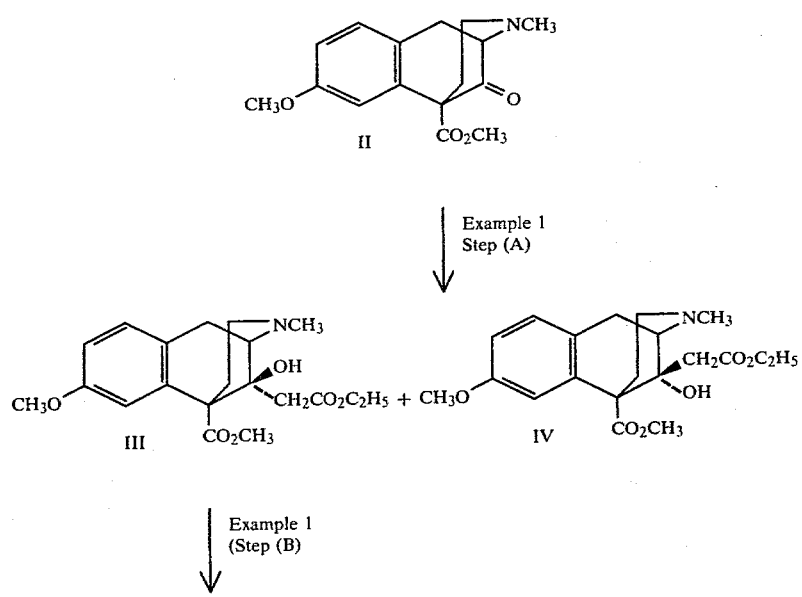

CHART I
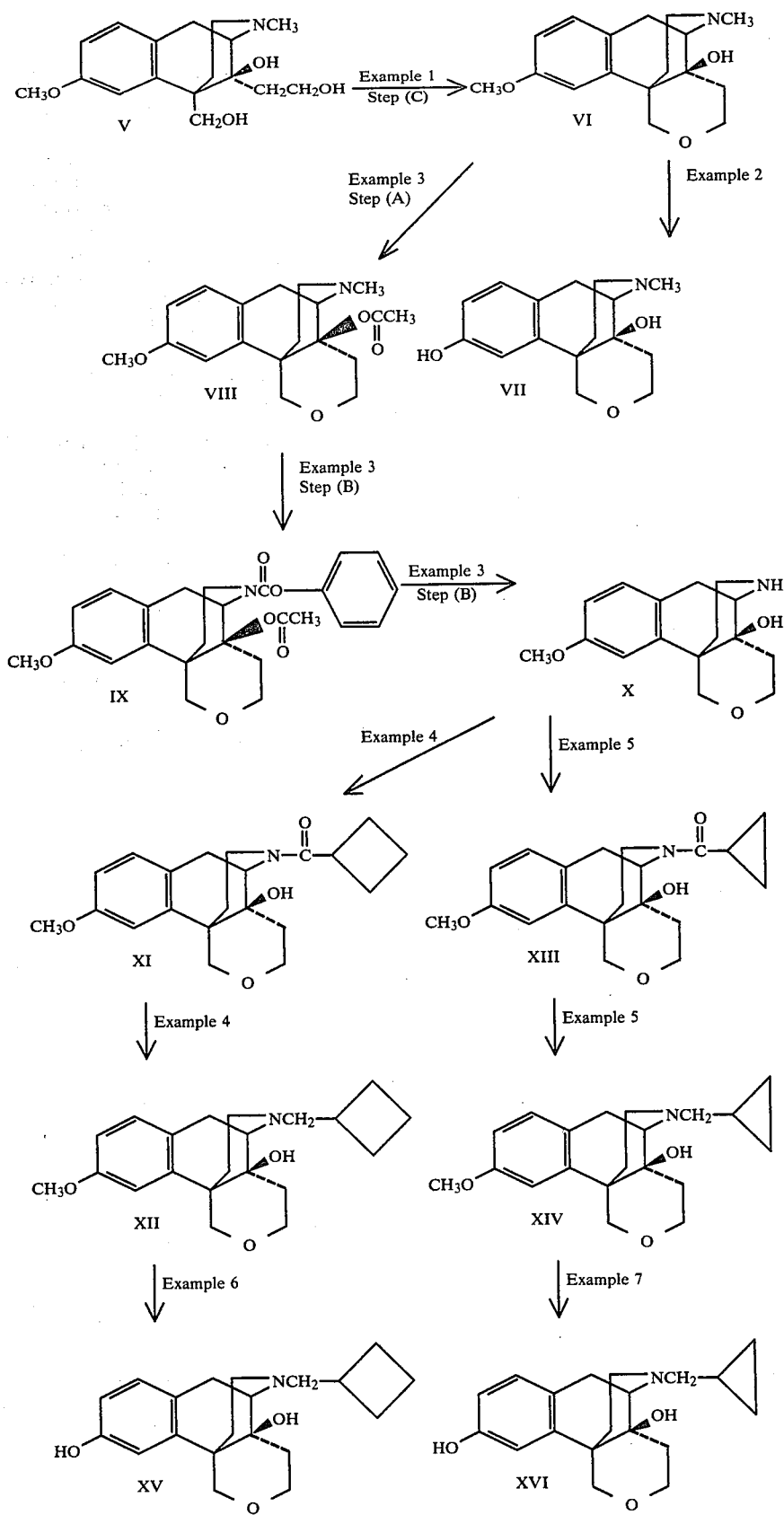
-continued

-continued
CHART I
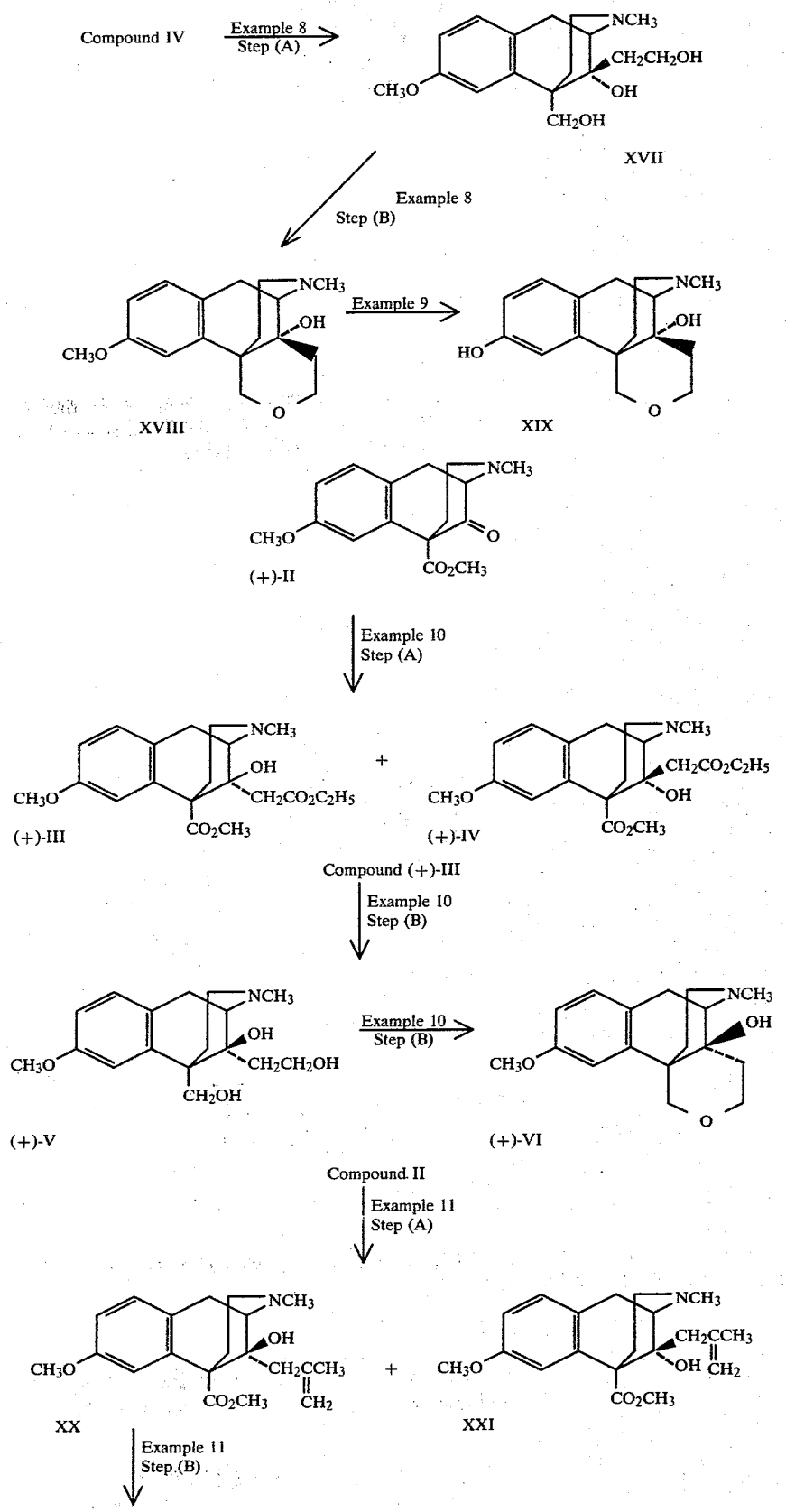

CHART I -continued

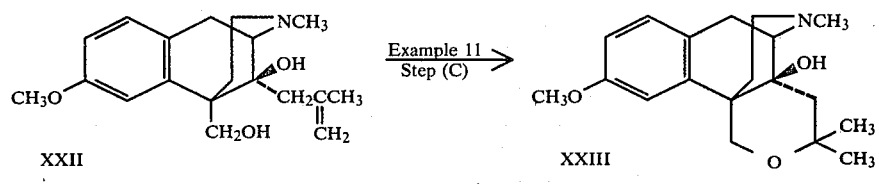

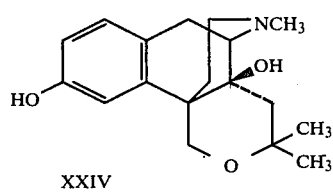

An alternative procedure for the preparation of intermediate Compound V from Compound II is as follows:

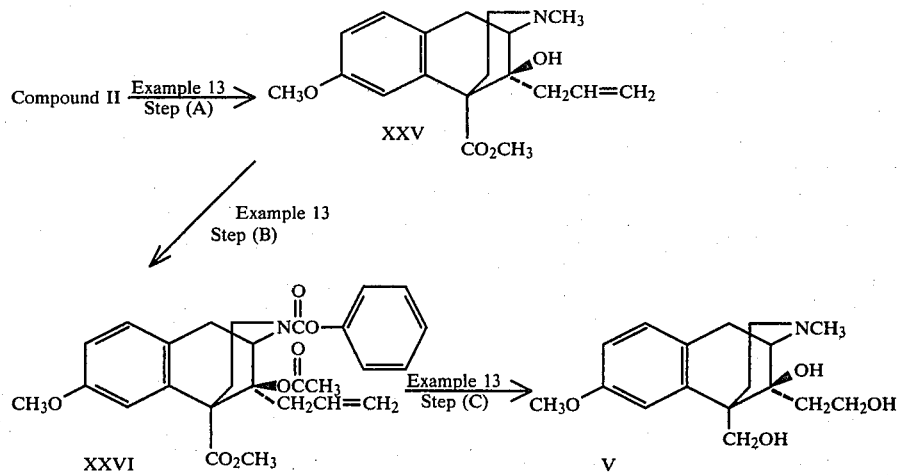

In another aspect, this invention relates to a process for the preparation of substituted 6-oxamorphinans and 6-oxaisomorphinans of the formula

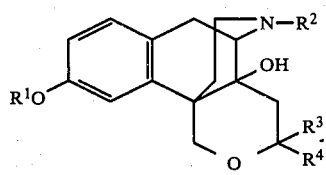 I wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl,

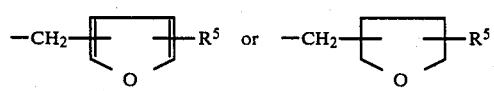

in which $R^5$ is hydrogen or (lower)alkyl, and $R^3$ and $R^4$ are the same or different and are hydrogen or (lower)alkyl, and pharmaceutically acceptable salts thereof, which process comprises the consecutive steps of (A) treating a compound of the formula

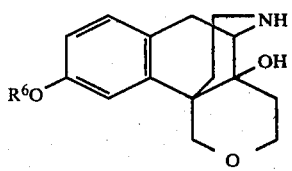 XXVII in which $R^6$ is (lower)alkyl with an alkylating or acylating agent of the formula

X—Z—W wherein W is hydrogen, (lower)alkyl, cyclopropyl, cyclobutyl,

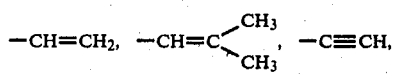

-continued

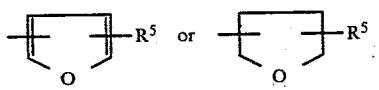

in which $R^5$ is hydrogen or (lower)alkyl; Z is

or —$CH_2$— and X is chloro, bromo or iodo; in an inert organic solvent, in the presence of an appropriate base, to produce a compound having the formula

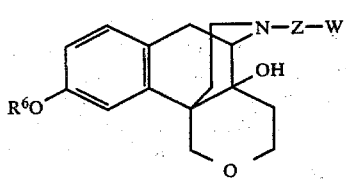
XXVIII in which $R^6$, Z and W are as defined above, and when Z is a carbonyl moiety (B) treating Compound XXVIII with a reducing agent selected from lithium aluminum hydride, aluminum hydride, diborane, and sodium bis(2-methoxyethoxy)aluminum hydride, in an inert organic solvent, to produce a compound having the formula

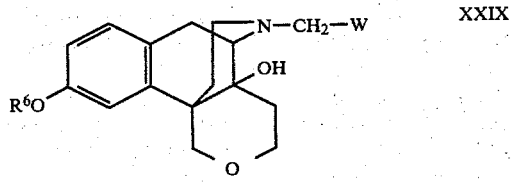
XXIX in which $R^6$ and W are as defined above, and when desired (C) cleaving the ether function of Compound XXVIII or XXIX with sodium thiomethoxide, sodium thioethoxide, lithium thiomethoxide, lithium thioethoxide, hydrobromic acid, boron tribromide or pyridine hydrochloride, to produce a compound having the formula

XXX in which Z and W are as defined above, and if desired (D) acylating Compound XXX with an acylating derivative of an acid of the formula $$R^7-\overset{O}{\underset{\|}{C}}-OH$$

in which $R^7$ is (lower)alkyl or 3-pyridyl, in an inert organic solvent, to produce a compound of the formula

XXXI in which $R^7$, Z and W are as defined above.

In starting material XXVII for the above process, $R^6$ is (lower)alkyl. In Chart I, above, the initial starting material (Compound II) contains a methoxy group in the corresponding position and thus produces the compound of Formula X, which also contains a methoxy group in the corresponding position (i.e. a compound of Formula XXVII in which $R^6$ is methyl), for use as the starting material in the above process. Compounds of Formula XXVII in which $R^6$ is (lower)alkyl other than methyl may be prepared by methods well known to those skilled in the art. For purposes of illustration, the following Chart II shows a procedure utilizing Compound IX to prepare a compound of Formula XXVII in which $R^6$ is ethyl. The corresponding propyl, butyl, etc. compounds may be prepared in a similar manner by utilizing the appropriate alkyl halide, e.g., propyl bromide, butyl bromide, etc.

Chart II

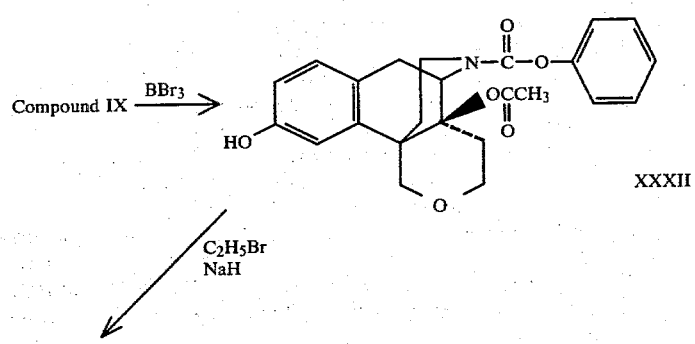

-continued

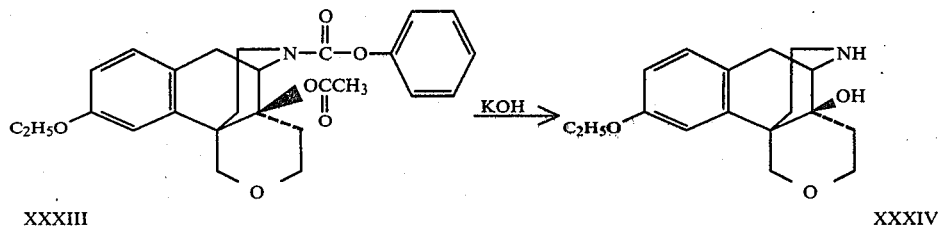

XXXIII                                              XXXIV

For the purpose of this disclosure the term "inert organic solvent" means an organic solvent that does not participate in the reaction to the extent that it emerges unchanged from the reaction. Suitable solvents for process Steps (A) and (D), above, include methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower)alkanols such as methanol, ethanol, n-propanol, isopropanol and the like.

Acceptable inert organic solvents for use in the reduction step (B) in the above process include among others, diethyl ether, dioxane, tetrahydrofuran, benzene, xylene, toluene and the like.

In cleavage step (C), above, suitable solvents will be apparent to those skilled in the art. Thus, when using sodium thiomethoxide, lithium thiomethoxide, sodium thioethoxide or lithium thioethoxide, suitable solvents include dimethylformamide, toluene, xylene, hexamethylphosphoramide and the like. When using boron tribromide, suitable solvents include methylene chloride, ether, chloroform, dichloroethane, carbon tetrachloride and the like. Hydrobromic acid may be utilized, for example in aqueous solution (e.g. 48%) or in acetic acid solution. Pyridine hydrochloride may conveniently be used in excess, where it serves as its own solvent.

The term "appropriate base" includes inorganic bases such as NaOH, KOH, $K_2CO_3$, $Na_2CO_3$, $NaHCO_3$, $KHCO_3$, and the like, and those tertiary amines commonly employed as a proton acceptor in acylation reactions. Such amines are tri(lower)alkylamines, e.g. trimethylamine, triethylamine, and the like, pyridine, dimethylaniline, N-methylpiperidine, and the like.

For the purpose of this disclosure and the appended claims, the term (lower)alkyl is defined as a straight or branched chain alkyl group containing from 1 to 6 carbon atoms, e.g. methyl, propyl, isobutyl, etc.. The term (lower)alkanoyl is defined as a straight or branched chain alkanoyl radical containing from 2 to 6 carbon atoms, e.g. acetyl, propionyl, isobutyryl, etc.. The term pharmaceutically acceptable salt is defined as a salt of a compound of this invention with any of the inorganic or organic acids which are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric, tartaric, pamoic, lauric, stearic, palmitic, oleic, myristic, lauryl sulfuric, naphthalenesulfonic, linoleic or linolenic acid, or the like.

Salts of the free bases may be prepared by conventional means, e.g. by addition of the appropriate acid to a solution of the free base in ethanol, 1-propanol, 2-propanol, acetone-methanol, acetone-ethanol, or the like. Salts of the compounds may be converted to the free base by treatment of the salt with dilute $K_2CO_3$ or $Na_2CO_3$ and extraction with $CH_2Cl_2$. The extract is dried with $MgSO_4$, $Na_2SO_4$ or $K_2CO_3$ and then concentrated to give the free base (generally in 100% yield).

All of the compounds of this invention are novel and valuable for their properties as analgetic and/or narcotic antagonist agents, or as intermediates in the preparation of compounds having these biological properties. Some of these compounds also possess potent antitussive or ADH (anti diuretic hormone) inhibitory activity.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

Table 1 compares the agonist activity of two of the preferred embodiments of this invention with the agonist activity of butorphanol and morphine sulfate, in the standard phenylquinone-induced writhing test [E. A. Siegmund, et al., Proc. Soc. Biol. & Med., 95, 729 (1957)]. By the subcutaneous route in mice, BL-5961 and BL-6021 were each about 1.4 times more potent than butorphanol and were each about 7 times more potent than morphine sulfate. Orally, in mice, BL-5961 was about 2.5 times as potent as butorphanol and about 1.4 times as potent as morphine sulfate. Subcutaneously, in rats, BL-5961 was about equipotent to butorphanol and about 4 times as potent as morphine sulfate.

TABLE 1

| Test Compound | Agonist Activity (ED50 in mg/kg) | | |
|---|---|---|---|
| | Mice (SC) | Mice (PO) | Rats (SC) |
| (±)-XV (BL-5961) | 0.037 | 2.2 | 0.041 |
| (±)-XXIV (BL-6021) | 0.037 | — | — |
| butorphanol | 0.051 | 5.6 | 0.040 |
| morphine sulfate | 0.26 | 3.1 | 0.16 |

Table 2 compares the oxymorphone and morphine antagonist activity of two of the preferred embodiments of this invention with the antagonist activity of butorphanol, in the standard oxymorphone-induced Straub tail test and the morphine antagonist rat tail flick test. In the Straub tail test, subcutaneously, BL-5951 and BL-5961 were about 5 times and about 1.6 times, respectively, as potent as butorphanol. Orally, they were about 55 times and about 1.7 times, respectively, as potent as butorphanol. In the rat tail flick test, subcutaneously, BL-5951 was about 4.8 times as potent as butorphanol, while BL-5961 was about equipotent to butorphanol.

TABLE 2

| Test Compound | Antagonist Activity (ED50 in mg/kg) | | |
|---|---|---|---|
| | Oxymorphone-induced Straub Tail | | Morphine Antagonist Rat Tail Flick |
| | SC | PO | SC |
| (±)-XVI (BL-5951) | ~0.2 | ~1 | ~0.09 |
| (±)-XV (BL-5961) | 0.61 | ~32 | ~0.4 |
| butorphanol | 0.98 | 55 | 0.43 |

This invention is illustrated by, but is in no way limited by, the following examples. All temperatures therein are given in ° Centigrade.

EXAMPLE 1

14β-Hydroxy-3-methoxy-17-methyl-6-oxamorphinan Hydrochloride (VI, BL-5872A)

(A)

11α-Carbethoxymethyl-6-carbomethoxy-11β-hydroxy-8-methoxy-3-methyl-1,2,3,4,5,6-hexahydro-2,6-methano-3-benzazocine Hydrogen Fumarate (III) and 11β-Carbethoxymethyl-6-carbomethoxy-11α-hydroxy-8-methoxy-3-methyl-1,2,3,4,5,6-hexahydro-2,6-methano-3-benzazocine Hydrogen Oxalate (IV)

To a cooled (−78°) solution of diisopropylamine (3.3 g; 0.033 m) in 40 ml of tetrahydrofuran (THF) under $N_2$ was added a solution of n-butyl lithium (15 ml of a 2.2 molar solution in n-hexane). After 5 minutes a solution of ethyl acetate (EtOAc) (2.9 g; 0.033 m) in 10 ml of THF was added. Ten minutes later a solution of 6-carbomethoxy-8-methoxy-3-methyl-11-oxo-1,2,3,4,5,6-hexahydro-2,6-methano-3-benzazocine (II) [prepared as described in U.S. Pat. No. 4,016,167] (8.7 g; 0.03 m) in 40 ml of THF was added. The reaction mixture was stirred at −78° for 1 hour then for 1 hour while allowing to warm to 0°. Water (50 ml) was added. The layers were separated and the aqueous layer was extracted with ether. The organic extracts were washed with saturated NaCl, dried ($Na_2SO_4$) and concentrated to leave an oil (12 g). Gas/liquid Chromatography (GLC) on this oil indicated it to contain ~69% β-OH isomer (III), ~19% α-OH isomer (IV) and ~6% starting material. This oil (7 g) was chromatographed on alumina (700 g grade III Woelm alumina—dry packed column). Elution with 9:1 (v/v) toluene-ethyl acetate (600 ml) gave 1.3 g of the pure α-OH isomer (IV). This was converted to a hydrogen oxalate salt in acetone-ethanol, mp 169°–171°.

Anal. calcd for $C_{20}H_{27}NO_6 \cdot C_2H_2O_4$: C, 56.52; H, 6.25; N, 3.00. Found: C, 56.55; H, 6.19; N, 3.01.

Further elution with 1:1 (v/v) toluene-ethyl acetate (200 ml) gave 4 g of the β-OH isomer (III). This was converted to a hydrogen fumarate salt in ethanol, mp 186°–187°.

Anal. calcd for $C_{20}H_{27}NO_6 \cdot C_4H_4O_4$: C, 58.41; H, 6.33; N, 2.84. Found: C, 58.49; H, 6.41; N, 2.76.

(B)

11β-Hydroxy-11α-(2-hydroxyethyl)-6-hydroxymethyl-8-methoxy-3-methyl-1,2,3,4,5,6-hexahydro-2,6-methano-3-benzazocine Hydrochloride (V)

A solution of III base (28.5 g; 0.075 m) in THF (200 ml) was added to a suspension of $LiAlH_4$ (8.75 g; 0.23 m) in THF (200 ml). The mixture was heated at reflux for 4 hours. After cooling, the mixture was cautiously treated with 27 ml of saturated $Na_2SO_4$ and 1 ml of 1 N NaOH, and stirred with warming until the solids were completely white. Solid $Na_2SO_4$ was added and the mixture was filtered through diatomaceous earth. The solids were dried and continuously extracted (Soxhlet extractor) with $CH_2Cl_2$. The combined THF filtrate and $CH_2Cl_2$ extract were concentrated to leave a crystalline residue (23 g; 99%) which gave a crystalline hydrochloride salt (2-propanol), mp 226°–229°.

Anal. calcd for $C_{17}H_{25}NO_4 \cdot HCl$: C, 59.38; H, 7.62; N, 4.07. Found: C, 59.33; H, 7.78; N, 4.01.

(C)

14β-Hydroxy-3-methoxy-17-methyl-6-oxamorphinan Hydrochloride (VI, BL-5872A)

A solution of V (22.5 g; 0.073 m) in 250 ml of 10 N $H_2SO_4$ was heated on a steam bath for 8 hours and then stored at 20° for 12 hours. The resultant solution was cautiously poured into a mixture of ice and concentrated $NH_4OH$ and extracted with $CH_2Cl_2$. Drying ($MgSO_4$) and concentration of the extract gave an oil (20.5 g) which was converted to a hydrochloride salt in 2-propanol (20.2 g; 82%), mp 182°–193°.

Anal. calcd for $C_{17}H_{23}NO_3 \cdot HCl \cdot (H_2O)_{\frac{1}{2}}$: C, 60.98; H, 7.52; N, 4.18; $H_2O$, 2.69. Found: C, 60.81; H, 7.38 N, 4.14; $H_2O$, 2.69.

EXAMPLE 2

3,14β-Dihydroxy-17-methyl-6-oxamorphinan Hydrogen Fumarate (VII, BL-5933F)

A mixture of VI (free base, from 0.67 g hydrochloride salt; 0.002 m), lithium thiomethoxide [see Tetrahedron Letters, 3859 (1977)] (3.5 g) and 40 ml of DMF was heated at reflux for 4 hours. The mixture was concentrated at reduced pressure. The residue was treated with water, acidified with hydrochloric acid and washed with ether. The aqueous solution was basified with $Na_2Co_3$ and extracted with $CH_2Cl_2$. Drying ($MgSO_4$) and concentration of the extracts gave an oil which crystallized on trituration with acetonitrile to give 0.48 g of product. This was converted to a hydrogen fumarate salt in 1-propanol, mp 235°–245° (dec).

Anal. calcd for $C_{16}H_{21}NO_3 \cdot C_4H_4O_4$: C, 61.37; H, 6.44; N, 3.58. Found: C, 61.52; H, 6.64; N, 3.43.

EXAMPLE 3

14β-Hydroxy-3-methoxy-6-oxamorphinan Hydrogen Fumarate (X, BL-5940F)

(A)

14β-Acetoxy-3-methoxy-17-methyl-6-oxamorphinan (VIII)

A mixture of VI (free base, from 18.5 g hydrochloride salt; 0.055 m) and acetic anhydride (160 ml) was heated on a steam bath for 4 hours. The acetic anhydride was removed at reduced pressure. The residue was treated with dilute $K_2CO_3$ and extracted with $CH_2Cl_2$. Drying ($MgSO_4$) and concentration of the extracts gave crystalline VIII (18.3 g; 100%), which was recrystallized from acetone, mp 161°–163°.

Anal. calcd for $C_{19}H_{25}NO_4$: C, 68.86; H, 7.60; N, 4.23. Found: C, 68.41; H, 7.80; N, 4.05 $H_2O$, 0.55.

(B) 14β-Hydroxy-3-methoxy-6-oxamorphinan Hydrogen Fumarate (X, BL-5940F)

A refluxing mixture of VIII (18.9 g; 0.057 m), $K_2CO_3$ (25 g) and toluene (200 ml) was treated with a solution of phenyl chloroformate (26.8 g; 0.17 m) in toluene (50 ml) over a period of 20 minutes. The mixture was heated at reflux for 24 hours. The cooled mixture was treated with 200 ml water, shaken well, and the layers separated. The toluene extract was washed with saturated NaCl, dried ($Na_2SO_4$) and concentrated to leave crude IX. This material was treated with 800 ml of 2-propanol, 200 ml of water and 96 g of KOH, and heated at reflux with stirring for 64 hours. The reaction mixture was concentrated, treated with water and extracted with $CH_2Cl_2$. Drying ($MgSO_4$) and concentration of the extracts gave the title product (X) as an oil which was converted to a hydrogen fumarate salt in 1-propanol (18.3 g; 82%), mp 230°–235° (dec).

Anal. calcd for $C_{16}H_{21}NO_3 \cdot C_4H_4O_4$: C, 61.37; H, 6.44; N, 3.58. Found: C, 61.42; H, 6.38; N, 3.65.

EXAMPLE 4

17-Cyclobutylmethyl-14β-hydroxy-3-methoxy-6-oxamorphinan Hydrochloride (XII, BL-5947A)

A solution of X (free base, from 3.1 g hydrogen fumarate salt; 0.008 m) in $CH_2Cl_2$ (30 ml) and 2 ml triethylamine was treated with a solution of cyclobutylcarbonyl chloride (1.2 g; 0.01 m) in 5 ml of $CH_2Cl_2$. After stirring for 2½ hours, the mixture was washed with dilute HCl, dried ($MgSO_4$) and concentrated to give XI as an oil. This oil was taken up in THF (20 ml) and added to a suspension of 0.9 g. of $LiAlH_4$ in 15 ml of THF. The mixture was heated at reflux for 16 hours. The cooled reaction mixture was cautiously treated with 2.7 ml of saturated $Na_2SO_4$ and a few drops 1 N NaOH, and warmed with stirring until the solids were completely white. The solids were removed by filtration and the filtrate was concentrated to give the product (XII) as an oil, which was converted to a hydrochloride salt in ethanol (2.7 g; 79%), mp 237°–250° (dec).

Anal. calcd for $C_{21}H_{29}NO_3 \cdot HCl$: C, 66.39; H, 7.96; N, 3.69. Corrected for 1.5% $H_2O$: C, 65.39; H, 8.01; N, 3.63; $H_2O$, 1.5. Found: C, 65.16; H, 7.91; N, 3.52; $H_2O$, 1.48.

EXAMPLE 5

17-Cyclopropylmethyl-14β-hydroxy-3-methoxy-6-oxamorphinan Hydrochloride (XIV, BL-5945A)

Compound XIII was prepared from X using a procedure similar to that used for preparing Compound XI in Example 4, but replacing the cyclobutylcarbonyl chloride by an equivalent amount of cyclopropylcarbonyl chloride. Compound XIII was reduced with $LiAlH_4$ by the procedure described in Example 4. The resulting Compound XIV was isolated as a hydrochloride salt from 2-propanol (77% yield), mp 256°–263° (dec).

Anal. calcd for $C_{20}H_{27}NO_3 \cdot HCl$: C, 65.65; H, 7.71; N, 3.83. C, 65.34; H, 7.64; N, 3.53.

EXAMPLE 6

17-Cyclobutylmethyl-3,14β-dihydroxy-6-oxamorphinan Hydrochloride (XV, BL-5961A)

Compound XII was O-demethylated with lithium thiomethoxide by a procedure similar to that described in Example 2. The resulting product (XV) was isolated as a hydrochloride salt from 2-propanol (60% yield), mp 263°–271° (dec). This material contains 5% 2-propanol (nmr estimate) which is not removed by drying at 100° at 0.04 mm pressure.

Anal. calcd for $C_{20}H_{27}NO_3 \cdot HCl$: C, 65.65; H, 7.71; N, 3.83. Corrected for 5% $C_3H_8O$ + 0.57% $H_2O$: C, 64.99, H, 8.01; N, 3.62; $H_2O$, 0.57. Found: C, 64.80; H, 7.82; N, 3.81; $H_2O$, 0.57.

EXAMPLE 7

17-Cyclopropylmethyl-3,14β-dihydroxy-6-oxamorphinan Hydrochloride (XVI, BL-5951A)

Compound XIV was O-demethylated with lithium thiomethoxide by a procedure similar to that described in Example 2. The resulting product (XVI) was isolated as a hydrochloride salt from 2-propanol (90% yield), mp 168°–195°.

Anal. calcd for $C_{19}H_{25}NO_3 \cdot HCl \cdot H_2O$: C, 61.69; H, 7.63; N, 3.79; $H_2O$, 4.86. Found: C, 61.42; H, 7.66; N, 3.91; $H_2O$, 4.63.

EXAMPLE 8

14α-Hydroxy-3-methoxy-17-methyl-6-oxaisomorphinan Hydrochloride (XVIII, BL-5918A)

(A)

11α-Hydroxy-11β-(2-hydroxyethyl)-6-hydroxymethyl-8-methoxy-3-methyl-1,2,3,4,5,6-hexahydro-2,6-methano-3-benzazocine Hydrochloride (XVII)

A solution of Compound IV base (7.4 g; 0.02 m) in THF (50 ml) was added to a suspension of $LiAlH_4$ (2.3 g; 0.06 m) in 50 ml THF. The mixture was heated at reflux for 4 hours. After cooling, the mixture was cautiously treated with 7 ml of saturated $Na_2SO_4$ and a few drops 1 N NaOH, and warmed with stirring until the solids were completely white. The solids were removed by filtration and the filtrate was concentrated to dryness. The resultant oily product (XVII) weighed 5.9 g. A portion of it was converted to a hydrochloride salt in 2-propanol, mp 201°–205° (dec).

Anal. calcd for $C_{17}H_{25}NO_4 \cdot HCl$: C, 59.38; H, 7.62; N, 4.07. Found: C, 59.47; H, 7.69; N, 4.14.

(B)

14α-Hydroxy-3-methoxy-17-methyl-6-oxaisomorphinan Hydrochloride (XVIII, BL-5918A)

Compound XVII (5.5 g; 0.018 m) was cyclized with 70 ml 10 N $H_2SO_4$ by a procedure similar to that described in Example 1, Step (C). The resulting product (XVIII) was isolated as hydrochloride salt from 2-propanol (4.6 g; 79% yield), mp 249°–253° (dec).

Anal. calcd for $C_{17}H_{23}NO_3 \cdot HCl$: C, 62.97; H, 7.42; N, 4.30. Found: C, 63.04; H, 7.48; N, 4.37.

EXAMPLE 9

3,14α-Dihydroxy-17-methyl-6-oxaisomorphinan Fumarate (XIX, BL-5937F)

Compound XVIII was O-demethylated with lithium thiomethoxide by a procedure similar to that described in Example 2. The product (XIX) was isolated as a fumarate salt from 1-propanol (67.4% yield), mp 247°–250° (dec.) This material contains one mole of 1-propanol solvate.

Anal. calcd for $(C_{16}H_{21}NO_3)_2 \cdot C_4H_4O_4 \cdot C_3H_8O$: C, 64.44; H, 7.49; N, 3.86. Found: C, 64.25; H, 7.79; N, 3.62.

EXAMPLE 10

(+)-14β-Hydroxy-3-methoxy-17-methyl-6-oxamorphinan [(+)-VI, BL-5875]

(A)

(+)-11α-Carbethoxymethyl-6-carbomethoxy-11β-hydroxy-8-methoxy-3-methyl-1,2,3,4,5,6-hexahydro-2,6-methano-3-benzazocine Hydrogen Oxalate [(+)-III] And
(+)-11β-Carbethoxymethyl-6-carbomethoxy-11α-hydroxy-8-methoxy-3-methyl-1,2,3,4,5,6-hexahydro-2,6-methano-3-benzazocine Hydrogen Oxalate [(+)-IV]

Compound (±)-II was resolved as described in Example 40 of U.S. Pat. No. 4,016,167 to produce (+)-II and (−)-II.

Compounds (+)-III and (+)-IV were prepared from (+)-II by a procedure similar to that described for Compounds III and IV in Example 1. Compound (+)-IV (11α-OH isomer) was isolated as a crystalline hydrogen oxalate from ethanol, mp 148°–150°.

Anal. calcd for $C_{20}H_{27}NO_6 \cdot C_2H_2O_4$: C, 56.52; H, 6.25; N, 3.00. Found: C, 56.67; H, 6.17; N, 3.08. Compound (+)-III (11β-OH isomer) was isolated as a crystalline hydrogen oxalate from ethanol, mp 175°–178°.

Anal. calcd for $C_{20}H_{27}NO_6 \cdot C_2H_2O_4$: C, 56.52; H, 6.25; N, 3.00. Found: C, 56.71; H, 6.18; N, 3.04.

(B)

(+)-14β-Hydroxy-3-methoxy-17-methyl-6-oxamorphinan [(+)-VI, BL-5875]

Compound (+)-III was reduced with $LiAlH_4$ in THF by a procedure similar to that described in Example 8, Step A. The product [(+)-V] was isolated as a hydrochloride salt from 2-propanol, mp 250°–255°. A suspension of Compound (+)-V (1.4 g; 0.004 m) in 85% $H_3PO_4$ (30 ml) was heated at 100° for 8 hours. The reaction mixture was poured into water, basified with concentrated $NH_4OH$ and extracted with $CH_2Cl_2$. Drying ($MgSO_4$) and concentration of the extracts gave crystalline (+)-VI (1.1 g) which was recrystallized from 2-propanol, mp 108.5°–110°, $[\alpha]_D^{22}$ +58.7° (C, 0.88, $CH_3OH$).

Anal. Calcd for $C_{17}H_{23}NO_3$: C, 70.56; H, 8.01; N, 4.84. Found: C, 70.53; H, 7.99; N, 4.73.

EXAMPLE 11

14β-Hydroxy-3-methoxy-7,7,17-trimethyl-6-oxamorphinan Hydrochloride (XXIII, BL-6016A)

(A)

6-Carbomethoxy-11β-hydroxy-8-methoxy-3-methyl-11α-(2-methylallyl)-1,2,3,4,5,6-hexahydro-2,6-methano-3-benzazocine Hydrochloride (XX) And
6-Carbomethoxy-11α-hydroxy-8-methoxy-3-methyl-11β-(2-methylallyl)-1,2,3,4,5,6-hexahydro-2,6-methano-3-benzazocine Hydrogen Oxalate (XXI)

An ice-cooled mixture of magesium chips (30 g) in 50 ml of THF was treated with 5 ml of a solution of 2-methylallyl chloride (10 g; 0.11 mole) in 80 ml of THF. After the reaction started, the remainder of the solution was added over ½ hour period and the mixture was stirred with cooling for 1 hour more. The above Grignard reagent was filtered through glass wool and added to a solution of Compound II (17.4 g; 0.06 mole) in 120 ml of THF maintained at −45° C. (dry ice-$CH_3CN$ bath) over 15 minutes. After 1 hour at −45° C. the reaction was treated with 250 ml of 10% $NH_4Cl$ solution. The layers were separated and the aqueous layer extracted further with ether. Drying and concentration of the organic extracts gave an oil (21.5 g) containing ~55% of Compound XX. This material was taken up in 200 ml 1-propanol and treated with 7 g fumaric acid. The crystals (12.2 g) were collected and recrystallized from 1-propanol to give material of sufficient purity (>93%) for use in Step B. A small sample was converted to a hydrochloride salt and crystallized from 2-propanol-acetone for analysis, purity by GLC analysis >97%, mp 196°–200°.

Anal. calcd for $C_{20}H_{27}NO_4 \cdot HCl$: C, 62.90; H, 7.39; N, 3.67. Found: C, 62.68; H, 7.26; N, 3.65.

The mother liquors from the above experiment were concentrated, treated with dilute $K_2CO_3$ and extracted with $CH_2Cl_2$ to give an oil containing Compounds XX and XXI, and an unknown product. Chromatography of a portion of this mixture on grade II neutral alumina using 95% toluene: 5% ethyl acetate for elution afforded a sample of Compound XXI which was converted to a hydrogen oxalate salt in acetone, mp 172°–174°.

Anal. calcd for $C_{20}H_{27}NO_4 \cdot C_2H_2O_4$: C, 60.68; H, 6.71; N, 3.22. Found: C, 60.32; H, 6.83; N, 3.01.

(B)

11β-Hydroxy-6-hydroxymethyl-8-methoxy-3-methyl-11α-(2-methylallyl)-1,2,3,4,5,6-hexahydro-2,6-methano-3-benzazocine Fumarate (XXII)

A solution of Compound XX (1.03 g; 0.003 mole) in THF (10 ml) was added to a mixture of $LiAlH_4$ (0.34 g) in THF (10 ml) and heated at reflux for 4 hours. This was cautiously treated with 1 ml of saturated $Na_2SO_4$ containing some NaOH and stirred, with warming, until the solids were white. The solids were removed by filtration and the filtrate was concentrated. The resultant oil was converted to a fumarate salt in 1-propanol, mp 186°–188°.

Anal. calcd for $(C_{19}H_{27}NO_3)_2 \cdot C_4H_4O_4$: C, 67.17; H, 7.79; N, 3.73. Found: C, 67.03; H, 7.91; N, 3.67.

(C)

14β-Hydroxy-3-methoxy-7,7,17-trimethyl-6-oxamorphinan Hydrochloride (XXIII, BL-6016A)

A solution of Compound XXII base (17 g; 0.053 mole) in 180 ml of 10 N $H_2SO_4$ was heated on a steam bath for 6 hours, then stored at 20° for 16 hours. The reaction mixture was cautiously poured into a mixture of ice-concentrated $NH_4OH$ (150 ml) and extracted with $CH_2Cl_2$. Drying and concentration of the extract gave XXIII as an oil (16.3 g) which was converted to a hydrochloride salt in 2-propanol (87% yield), mp 184°–185°.

Anal. calcd for $C_{19}H_{27}NO_3 \cdot HCl$: C, 64.48; H, 7.97; N, 3.96. Found: C, 64.15; H, 7.95; N, 4.06.

EXAMPLE 12

3,14β-Dihydroxy-7,7,17-trimethyl-6-oxamorphinan (XXIV, BL-6021)

A mixture of Compound XXIII base (0.002 mole) and sodium thioethoxide (0.03 mole) (prepared from sodium hydride and ethyl mercaptan) in 40 ml of dimethyl formamide (DMF) was heated at reflux under nitrogen for 3½ hours. The solvent was removed at reduced pressure. The residue was treated with water, acidified with 6 N hydrochloric acid and washed with ether. The aqueous layer was filtered, basified with concentrated ammonium hydroxide and extracted with CH₂Cl₂. Concentration of the extracts gave crystalline XXIV which was recrystallized from ethanol (62% yield), mp 232°–233°.

Anal. calcd for C₁₈H₂₅NO₃: C, 71.25; H, 8.31; N, 4.62. Found: C, 71.35; H, 8.45; N, 4.58.

EXAMPLE 13

Alternate Method of Preparation of 11β-Hydroxy-11α-(2-hydroxyethyl)-6-hydroxymethyl-8-methoxy-3-methyl-1,2,3,4,5,6-hexahydro-2,6-methano-3-benzazocine Hydrochloride (V)

(A)

11α-Allyl-6-carbomethoxy-11β-hydroxy-8-methoxy-3-methyl-1,2,3,4,5,6-hexahydro-2,6-methano-3-benzazocine (XXV)

A cooled (0°) solution of Compound II (23.3 g; 0.05 m) in THF (120 ml) was treated with allyl magnesium chloride (50 ml of 1.2 M solution in THF; 0.6 m). The mixture was allowed to warm to room temperature (21°) and stirred for 64 hours. The reaction mixture was treated with a solution of NH₄Cl (20 g) in 100 ml water. The layers were separated and the THF extract was washed with saturated NaCl, dried (Na₂SO₄) and concentrated. The resultant oil (16 g) contained ~60% β-OH isomer (XXV), ~20% α-OH isomer, and ~15% starting ketone (II) by GLC analysis. This material was purified by crystallization of a hydrogen oxalate salt (acetone-material) followed by crystallization of the free base (6.4 g; 39% yield), mp 111°–112°. GLC analysis indicated this material to be >99% of the desired Compound XXV.

Anal. calcd for C₁₉H₂₅NO₄: C, 68.86; H, 7.60; N, 4.23. Found: C, 68.58; H, 7.71; N, 4.02.

(B)

11β-Acetoxy-11α-allyl-6-carbomethoxy-3-carbophenoxy-8-methoxy-1,2,3,4,5,6-hexahydro-2,6-methano-3-benzazocine (XXVI)

A solution of XXV (6.3 g; 0.018 m) in acetic anhydride (60 ml) was heated at 100° for 4 hours. After allowing the reaction to cool to room temperature overnight (16 hours), the mixture was concentrated. The residue was treated with dilute K₂CO₃ and extracted with CH₂Cl₂. The extracts were dried (MgSO₄) and concentrated to give the acetoxy derivative of XXV (7.2 g). A refluxing mixture of this material in toluene (70 ml) and K₂CO₃ (12 g) was treated with a solution of phenylchloroformate (8.6 g; 0.055 m) in toluene (30 ml). Refluxing was continued for 40 hours. After cooling, the mixture was washed with water and saturated NaCl. The toluene extract was dried (MgSO₄) and concentrated to an oil (13 g). This oil was chromatographed on silica gel (400 g). Elution with CH₂Cl₂ (1L) removed several impurities. Further elution with EtOAc (500 ml) gave the desired product (XXVI) which was crystallized from methanol (5.5 g; 63% yield), mp 106°–109°.

Anal. calcd for C₂₇H₂₉NO₇: C, 67.63; H, 6.10; N, 2.92. C, 67.51; H, 6.06; N, 2.91.

(C)

11β-Hydroxy-11α-(2-hydroxyethyl)-6-hydroxymethyl-8-methoxy-3-methyl-1,2,3,4,5,6-hexahydro-2,6-methano-3-benzazocine Hydrochloride (X)

A solution of XXVI (5.3 g; 0.011 m) in CH₂Cl₂ (40 ml) and CH₃OH (20 ml) was cooled to −78°. Ozone (approx. 0.013 m) was bubbled into this solution over a period of 70 minutes. A stream of N₂ was then bubbled through the solution for 15 minutes to remove excess ozone. Dimethyl sulfide (3 ml) was added and the mixture was allowed to slowly warm to room temperature (21°), then stirred at 21° and 16 hours. The reaction was concentrated to near dryness, taken up in CH₃OH (35 ml) and 4 N HCl (15 ml) (slight warming needed) and stirred for 4 hours. After concentration, the residue was treated with dilute K₂CO₃ and extracted with CH₂Cl₂. Drying (MgSO₄) and concentration of the extracts gave an amorphous solid (6 g). This material was taken up in THF (30 ml) and reduced with LiAlH₄ (3 g) in THF (30 ml) by a procedure similar to that described in Example 1. Compound V was isolated as a crystalline hydrochloride (1.3 g; 33% yield).

EXAMPLE 14

3-Acetoxy-17-cyclopropylmethyl-14β-hydroxy-6-oxamorphinan

Equimolar quantities of 17-cyclopropylmethyl-3,14β-dihydroxy-6-oxamorphinan (XVI), acetyl chloride and pyridine are mixed together in dry methylene chloride and the resultant mixture is heated at reflux for several hours to produce the title compound.

EXAMPLE 15

17-Cyclopropylmethyl-14β-hydroxy-3-nicotinoyloxy-6-oxamorphinan

Equimolar amounts of 17-cyclopropylmethyl-3,14β-dihydroxy-6-oxamorphinan (XVI), nicotinoyl chloride hydrochloride and pyridine are mixed together in dry methylene chloride and the mixture is heated at reflux for 3 hours to produce the title compound.

EXAMPLE 16

17-Allyl-3,14β-dihydroxy-6-oxamorphinan (A) 17-Allyl-14β-hydroxy-3-methoxy-6-oxamorphinan A mixture of 3-methoxy-14β-hydroxy-6-oxamorphinan (X) (0.005 m), allyl bromide (0.006 m) and potassium carbonate (2 g) in 20 ml acetonitrile is heated at reflux for 18 hours. The mixture is filtered and the filtrate concentrated. The residue is treated with water and extracted with ethyl acetate. The extracts are dried (Na₂SO₄) and concentrated to give the title compound.

(B) 17-Allyl-3,14β-dihydroxy-6-oxamorphinan

The product of Step (A) is demethylated by the general procedure of Example 2 to produce the title product.

EXAMPLE 17

3,14β-Dihydroxy-17-(3′,3′-dimethylallyl)-6-oxamorphinan

The general procedure of Example 16, Steps (A) and (B), is repeated, except that the allyl bromide utilized therein is replaced by an equimolar amount of 3,3-dimethylallyl bromide, and the title compound is thereby produced.

EXAMPLE 18

14β-Hydroxy-3-methoxy-7,7-dimethyl-6-oxamorphinan Hydrogen Fumarate

The general procedure of Example 3, Steps (A) and (B), are repeated except that the 14β-hydroxy-3-methoxy-17-methyl-6-oxamorphinan (VI) free base utilized therein as starting material is replaced by an equimolar amount of the free base of 14β-hydroxy-3-methoxy-7,7,17-trimethyl-6-oxamorphinan (XXIII) prepared in Example 11, and the title compound is thereby produced.

EXAMPLE 19

17-Cyclobutylmethyl-14β-hydroxy-3-methoxy-7,7-dimethyl-6-oxamorphinan Hydrochloride The general procedure of Example 4 is repeated except that the 14β-hydroxy-3-methoxy-6-oxamorphinan (X) free base utilized therein as starting material is replaced by an equimolar amount of the free base of 14β-hydroxy-3-methoxy-7,7-dimethyl-6-oxamorphinan, and the title compound is thereby produced.

EXAMPLE 20

17-Cyclobutylmethyl-3,14β-dihydroxy-7,7-dimethyl-6-oxamorphinan Hydrochloride

The general procedure of Example 6 is repeated except that the 17-cyclobutylmethyl-14β-hydroxy-3-methoxy-6-oxamorphinan utilized therein as starting material is replaced by an equimolar amount of 17cyclobutylmethyl-14β-hydroxy-3-methoxy-7,7-dimethyl-6-oxamorphinan, and the title compound is thereby produced.

EXAMPLE 21

17-Cyclopropylmethyl-14β-hydroxy-3-methoxy-7,7-dimethyl-6-oxamorphinan Hydrochloride The general procedure of Example 5 is repeated except that the 14β-hydroxy-3-methoxy-6-oxamorphinan (X) free base utilized therein as starting material is replaced by an equimolar amount of the free base of 14β-hydroxy-3-methoxy-7,7-dimethyl-6-oxamorphinan, and the title compound is thereby produced.

EXAMPLE 22

17-Cyclopropylmethyl-3,14β-dihydroxy-7,7-dimethyl-6-oxamorphinan Hydrochloride

The general procedure of Example 7 is repeated except that the 17-cyclopropylmethyl-14β-hydroxy-3-methoxy-6-oxamorphinan utilized therein as starting material is replaced by an equimolar amount of 17-cyclopropylmethyl-14β-hydroxy-3-methoxy-7,7-dimethyl-6-oxamorphinan, and the title compound is thereby produced.

EXAMPLE 23

(−)-14β-Hydroxy-3-methoxy-17-methyl-6-oxamorphinan [(−)-VI]

(A)

(−)-11α-Carbethoxymethyl-6-carbomethoxy-11β-hydroxy-8-methoxy-3-methyl-1,2,3,4,5,6-hexahydro-2,6-methano-3-benzazocine Hydrogen Oxalate [(−)-III] And
(−)-11βCarbethoxymethyl-6-carbomethoxy-11α-hydroxy-8-methoxy-3-methyl-1,2,3,4,5,6-hexahydro-2,6-methano-3-benzazocine Hydrogen Oxalate [(−)-IV]

The general procedure of Example 10 Step (A) is repeated except that the Compound (+)-II utilized therein as starting material is replaced by an equimolar amount of Compound (−)-II, and the title compounds are produced.

(B)

(−)-14β-Hydroxy-3-methoxy-17-methyl-6-oxamorphinan [(−)-VI]

The general procedure of Example 10 Step (B) is repeated except that the Compound (+)-III utilized therein as starting material is replaced by an equimolar amount of Compound (−)-III, and the title compound is produced.

EXAMPLE 24

Spiro[cyclohexane-1,7′-(14′β-hydroxy-3′-methoxy-17′-methyl-6′-oxamorphinan)] (XXXVIII)

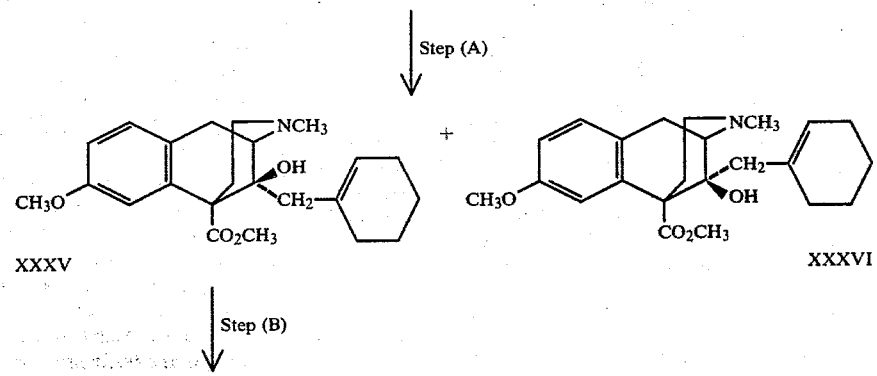

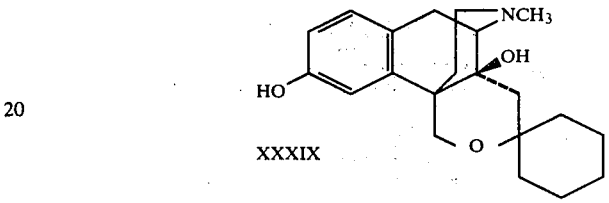

(A)
6-Carbomethoxy-11α-(1-cyclohexenylmethyl)-11β-hydroxy-8-methoxy-3-methyl-1,2,3,4,5,6-hexahydro-2,6-methano-3-benzazocine (XXXV) And
6-Carbomethoxy-11β-(1-cyclohexenylmethyl)-11α-hydroxy-8-methoxy-3-methyl-1,2,3,4,5,6-hexahydro-2,6-methano-3-benzazocine (XXXVI)

An ice-cooled mixture of magnesium chips (30 g) in 50 ml of THF is treated with 5 ml of a solution of 1-chloromethylcyclohexene (14.4 g; 0.11 mole) [Bull. Chem. Soc. Japan, 44, 1885 (1971)] in 80 ml of THF. After the reaction starts, the remainder of the solution is added over a period of 30 minutes, and stirring is continued for 1 hour longer. This Grignard reagent is filtered through glass wool and added to a solution of Compound II (17.4 g; 0.06 mole) in 120 ml of THF maintained at −45° C. (dry ice-acetonitrile bath) over a period of 15 minutes. After 1 hour at −45° C., the reaction is treated with 250 ml of 10% NH₄Cl solution. The organic layer is separated, dried and concentrated to dryness to afford a mixture of Compounds XXXV and XXXVI. This mixture is separated by chromatography on Grade II alumina.

(B)
11α-(1-Cyclohexenylmethyl)-11β-hydroxy-6-hydroxymethyl-8-methoxy-3-methyl-1,2,3,4,5,6-hexahydro-2,6-methano-3-benzazocine (XXXVII)

The general procedure of Example 11 Step (B) is repeated except that the Compound XX utilized therein as starting material is replaced by an equimolar amount of Compound XXXV from Step (A), above, and the title compound is thereby produced.

(C)
Spiro[cyclohexane-1,7'-(14'β-hydroxy-3'-methoxy-17'-methyl-6'-oxamorphinan)] (XXXVIII)

The general procedure of Example 11 Step (C) is repeated except that the Compound XXII utilized therein as starting material is replaced by an equimolar amount of Compound XXXVII from Step (B), above, and the title compound is thereby produced.

EXAMPLE 25

Compound XXXVIII ⟶

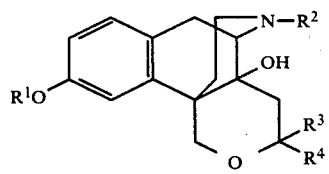

Spiro[cyclohexane-1,7'-(3',14'β-dihydroxy-17'-methyl-6'-oxamorphinan)] (XXXIX)

The general procedure of Example 12 is repeated except that the Compound XXIII utilized therein as starting material is replaced by an equimolar amount of Compound XXXVIII prepared in Example 24, above, and the title compound is thereby produced.

We claim:

1. A compound of the formula

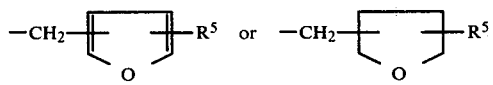

wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl, $$-CH_2-\boxed{\phantom{xx}}-R^5 \quad \text{or} \quad -CH_2-\boxed{\phantom{xx}}-R^5$$

in which $R^5$ is hydrogen or (lower)alkyl, and $R^3$ and $R^4$ are the same or different and are hydrogen or (lower)alkyl, or $R^3$ and $R^4$, when taken together, represent an alkylene group of from 2 to 6 carbon atoms; or a pharmaceutically acceptable salt thereof.

2. A compound of claim 1 wherein $R^1$ is hydrogen or (lower)alkyl, $R^2$ is hydrogen, (lower)alkyl, cyclopropylmethyl or cyclobutylmethyl, and $R^3$ and $R^4$ are the same or different and are hydrogen or (lower)alkyl, or a pharmaceutically acceptable salt thereof.

3. A compound of claim 1 wherein $R^1$ is hydrogen or methyl, $R^2$ is hydrogen, methyl, cyclopropylmethyl or cyclobutylmethyl, and $R^3$ and $R^4$ are the same or different and are hydrogen or methyl, or a pharmaceutically acceptable salt thereof.

4. A compound of claim 1 wherein $R^1$, $R^3$ and $R^4$ are hydrogen and $R^2$ is cyclopropylmethyl, or a pharmaceutically acceptable salt thereof.

5. A compound of claim 1 wherein $R^1$, $R^3$ and $R^4$ are hydrogen and $R^2$ is cyclobutylmethyl, or a pharmaceutically acceptable salt thereof.

6. A compound of claim 1 wherein $R^1$ is hydrogen and $R^2$, $R^3$ and $R^4$ are methyl, or a pharmaceutically acceptable salt thereof.

7. 17-Cyclopropylmethyl-3,14β-dihydroxy-6-oxamorphinan or a pharmaceutically acceptable salt thereof.

8. The (−)-isomer of the compound of claim 7 or a pharmaceutically acceptable salt thereof.

9. 17-Cyclobutylmethyl-3,14β-dihydroxy-6-oxamorphinan or a pharmaceutically acceptable salt thereof.

10. The (−)-isomer of the compound of claim 9 or a pharmaceutically acceptable salt thereof.

11. 3,14β-Dihydroxy-7,7,17-trimethyl-6-oxamorphinan or a pharmaceutically acceptable salt thereof.

12. The (−)-isomer of the compound of claim 11 or a pharmaceutically acceptable salt thereof.

13. 7-Cyclobutylmethyl-3,14β-dihydroxy-7,7-dimethyl-6-oxamorphinan or a pharmaceutically acceptable salt thereof.

14. The (−)-isomer of the compound of claim 13 or a pharmaceutically acceptable salt thereof.

15. 7-Cyclopropylmethyl-3,14β-dihydroxy-7,7-dimethyl-6-oxamorphinan or a pharmaceutically acceptable salt thereof.

16. The (−)-isomer of the compound of claim 15 or a pharmaceutically acceptable salt thereof.

* * * * *